(12) United States Patent
Sloss et al.

(10) Patent No.: US 9,217,723 B2
(45) Date of Patent: Dec. 22, 2015

(54) CO-FACIAL ANALYTICAL TEST STRIP WITH STACKED UNIDIRECTIONAL CONTACT PADS

(75) Inventors: Scott Sloss, Inverness (GB); Russell Bain, Inverness (GB); Graeme Webster, Inverness (GB)

(73) Assignee: Cilag GmbH International, Zug (CH)

( * ) Notice: Subject to any disclaimer, the term of this patent is extended or adjusted under 35 U.S.C. 154(b) by 940 days.

(21) Appl. No.: 13/410,609

(22) Filed: Mar. 2, 2012

(65) Prior Publication Data

US 2013/0228474 A1 Sep. 5, 2013

(51) Int. Cl.
*G01N 27/327* (2006.01)

(52) U.S. Cl.
CPC .................................. *G01N 27/3272* (2013.01)

(58) Field of Classification Search
CPC ........... G01N 27/327–27/3272; G01N 33/543; C12Q 1/00; C12Q 1/54
USPC ............. 204/403.01–403.15; 205/775, 775.5, 205/792
See application file for complete search history.

(56) References Cited

U.S. PATENT DOCUMENTS

| | | | |
|---|---|---|---|
| 5,082,626 A | 1/1992 | Grage, Jr. | |
| 6,071,391 A * | 6/2000 | Gotoh et al. | 204/403.05 |
| 6,212,417 B1 | 4/2001 | Ikeda et al. | |
| 7,343,188 B2 | 3/2008 | Sohrab | |
| 7,390,665 B2 | 6/2008 | Gilmour et al. | |
| 7,967,140 B2 | 6/2011 | Grossman | |
| 2003/0102213 A1 | 6/2003 | Gotoh et al. | |
| 2004/0020771 A1 | 2/2004 | Taniike et al. | |
| 2004/0253367 A1 | 12/2004 | Wogoman | |
| 2005/0258035 A1 | 11/2005 | Harding et al. | |
| 2006/0226985 A1 | 10/2006 | Goodnow et al. | |
| 2007/0037057 A1 | 2/2007 | Douglas | |

(Continued)

FOREIGN PATENT DOCUMENTS

| | | |
|---|---|---|
| CN | 1134659 C | 1/2004 |
| CN | 1975403 A | 6/2007 |

(Continued)

OTHER PUBLICATIONS

International Search Report, PCT Application No. PCT/EP2013/054222, dated May 3, 2013, 3 pages, European Patent Office, Rijswijk, Netherlands.

(Continued)

*Primary Examiner* — J. Christopher Ball
*Assistant Examiner* — Maris R Kessel

(57) ABSTRACT

An analytical test strip ("ATT") for use with a test meter includes a first insulating layer, with a first insulating layer upper surface, and a first electrically conductive layer ("ECL") disposed thereon. The first ECL includes a first electrode portion ("EP") and an electrical contact pad in electrical communication with the first EP. The ATT also includes a patterned spacer layer disposed above the first ECL that includes (i) a distal portion defining a bodily fluid sample-receiving chamber therein that overlies the first EP and (ii) an insulating proximal portion with an upper surface having a second ECL disposed thereon. The second ECL includes an interlayer contact portion and an electrical contact pad. A third ECL of the ATT includes a second EP and a proximal portion that overlies the interlayer contact portion. The second EP is disposed overlying and exposed to the sample-receiving chamber in an opposing relationship to the first EP.

5 Claims, 7 Drawing Sheets

(56) References Cited

U.S. PATENT DOCUMENTS

| | | |
|---|---|---|
| 2007/0074977 A1 | 4/2007 | Guo et al. |
| 2009/0024015 A1 | 1/2009 | Curry |
| 2009/0026074 A1* | 1/2009 | Iyengar .................. 204/400 |
| 2009/0095623 A1 | 4/2009 | Boiteau et al. |
| 2009/0317297 A1* | 12/2009 | Mahoney et al. ............. 422/56 |
| 2009/0325205 A1 | 12/2009 | Fujii et al. |
| 2010/0017165 A1 | 1/2010 | Zhong |
| 2011/0070634 A1 | 3/2011 | Takahashi et al. |

FOREIGN PATENT DOCUMENTS

| | | |
|---|---|---|
| CN | 101424684 A | 5/2009 |
| CN | 101779120 A | 7/2010 |
| EP | 1347058 A2 | 9/2003 |
| EP | 1642646 A1 | 4/2005 |
| EP | 2138846 A1 | 12/2009 |
| EP | 2317315 A1 | 5/2011 |
| JP | H11 051895 A | 2/1999 |
| JP | 11094817 A | 4/1999 |
| WO | WO 2007/071562 A1 | 6/2007 |
| WO | 2011049094 A1 | 4/2011 |

OTHER PUBLICATIONS

International Search Report, PCT Application No. PCT/EP2013/054216, dated May 7, 2013, 3 pages, European Patent Office, Rijswijk, Netherlands.

International Preliminary Report on Patentability issued in related International Patent Application No. PCT/EP2013/054216, mailed Sep. 12, 2014, 8 pages.

International Preliminary Report on Patentability issued in related International Patent Application No. PCT/EP2013/054222, mailed Sep. 12, 2014, 12 pages.

Search Report issued in related Chinese Patent Application No. 201380012160.1, dated Jul. 27, 2015, 2 pages.

First Office Action issued in related Chinese Patent Application No. 201380012160.1, dated Aug. 5, 2015, 21 pages.

* cited by examiner

CO-FACIAL ANALYTICAL TEST STRIP WITH STACKED UNIDIRECTIONAL CONTACT PADS

BACKGROUND OF THE INVENTION

1. Field of the Invention

The present invention relates, in general, to medical devices and, in particular, to test meters and related methods.

2. Description of Related Art

The determination (e.g., detection and/or concentration measurement) of an analyte in a fluid sample is of particular interest in the medical field. For example, it can be desirable to determine glucose, ketone bodies, cholesterol, lipoproteins, triglycerides, acetaminophen and/or HbA1c concentrations in a sample of a bodily fluid such as urine, blood, plasma or interstitial fluid. Such determinations can be achieved using a hand-held test meter in combination with analytical test strips (e.g., electrochemical-based analytical test strips).

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

DETAILED DESCRIPTION OF ILLUSTRATIVE EMBODIMENTS

Figure 1:
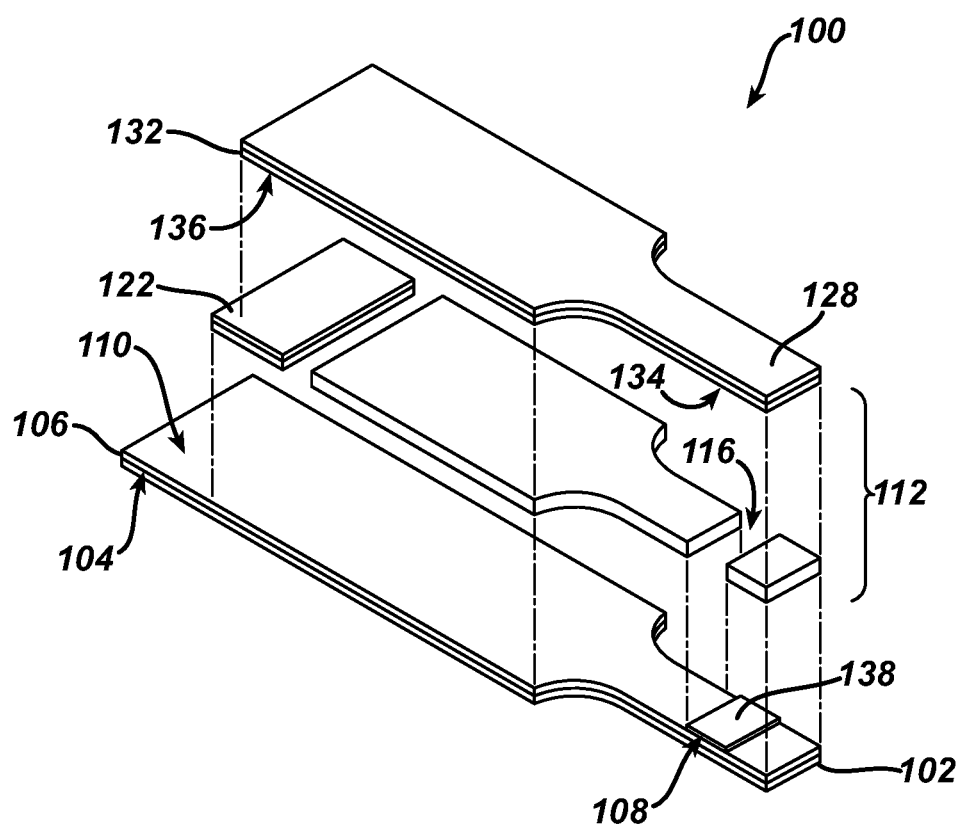
FIG. 1 is a simplified exploded perspective view of an analytical test strip according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

In general, analytical test strips for use with a test meter (such as a hand-held test meter) according to embodiments of the present invention include a first insulating layer with a first insulating layer upper surface and a first electrically conductive layer disposed on the first insulating layer upper surface. The first electrically conductive layer includes a first electrode portion (such as a working electrode portion) and an electrical contact pad in electrical communication with the first electrode portion. The analytical test strips also include a patterned spacer layer disposed above the first electrically conductive layer. The patterned spacer layer includes (i) a distal portion defining a bodily fluid sample-receiving chamber therein that overlies the first electrode portion and (ii) an insulating proximal portion with an upper surface having a second electrically conductive layer disposed thereon. The second electrically conductive layer includes an interlayer contact portion and an electrical contact pad in electrical communication with the interlayer contact portion.

The analytical test strips further include a second insulating layer that is disposed above the patterned spacer layer and has a second insulating layer lower surface with a third electrically conductive layer disposed thereon. The third electrically conductive layer includes a second electrode portion (such as, for example, a reference/counter electrode) and a proximal portion that overlies the interlayer contact portion.

In addition, the second electrode portion of the analytical test strips is disposed overlying and exposed to the sample-receiving chamber in an opposing (i.e., co-facial) relationship to the first electrode portion. Moreover, the proximal portion is operatively juxtaposed with the interlayer contact portion such that there is an electrical connection between the second electrode portion of the third electrically conductive layer and the electrical contact pad of the patterned spacer layer during use of the analytical test strip.

The electrical contact pad of the first electrically conductive layer and the electrical contact pad of the second electrically conductive layer are referred to as stacked unidirectional contact pads. They are "stacked" since the electrical contact pad of the second electrically conductive layer is elevated with respect to the electrical contact pad of the first electrically conductive layer. They are "unidirectional" since both are on upper surfaces and can, therefore, be accessed and contacted from the same direction.

Analytical test strips according to the present invention are beneficial in that, for example, their configuration and, in particular, the stacked unidirectional nature of the contact pads, is amenable to high-volume, high-yield mass production without dedicated and complex tight-alignment die cutting steps to expose the contact pads.

Figure 2:
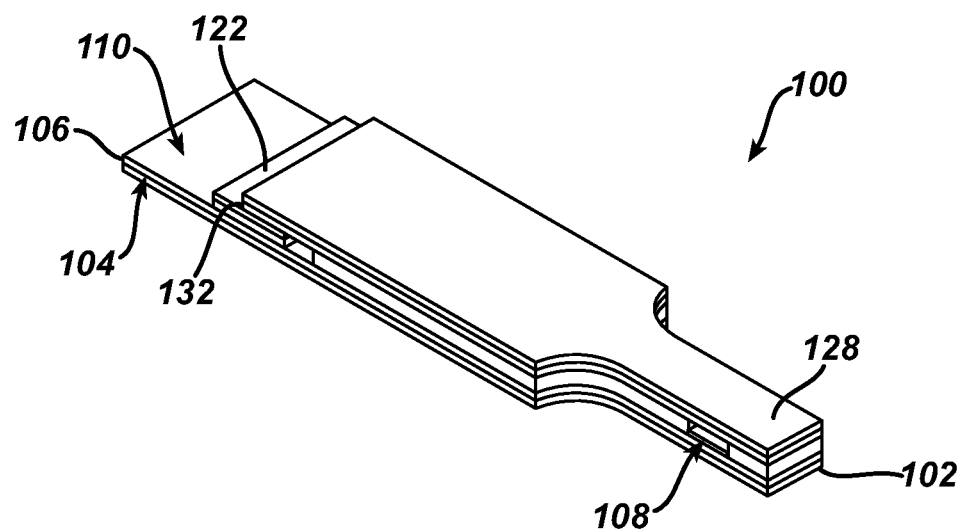
FIG. 2 is a simplified perspective view of the analytical test strip of FIG. 1.
Figure 3:
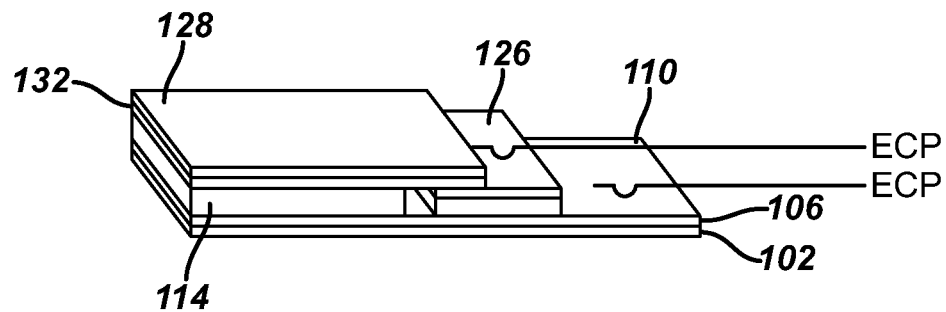
FIG. 3 is a simplified perspective view of a distal portion of the analytical test strip of FIG. 1 in contact with test meter electrical connector pins.
Figure 4:
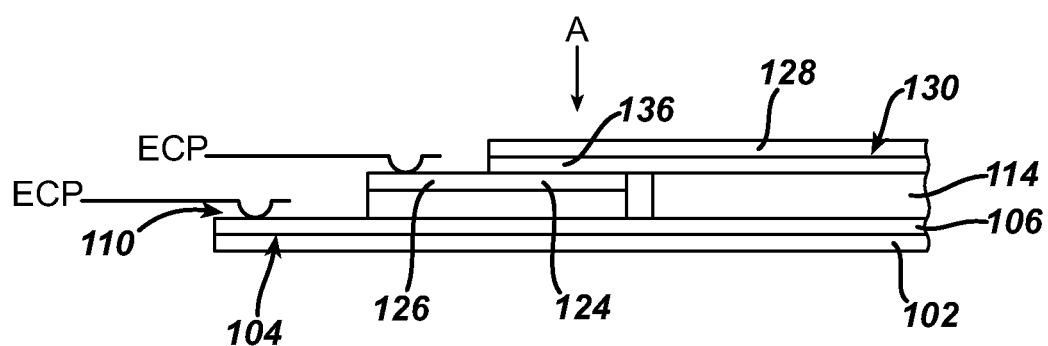
FIG. 4 is a simplified side view of the distal portion of FIG. 3.
Figure 5:
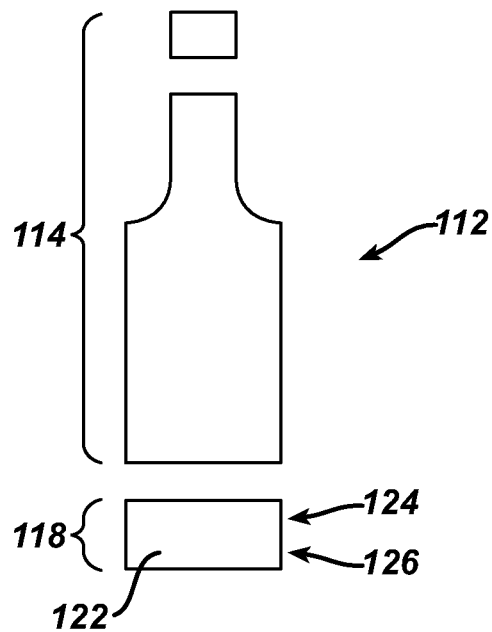
FIG. 5 is a top view of a patterned spacer layer of the analytical test strip of FIG. 1.
Figure 6:
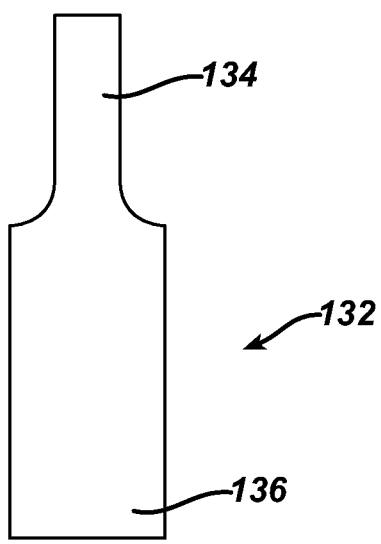
FIG. 6 is a top view of a third electrically conductive layer of the analytical test strip of FIG. 1.

FIG. 1 is a simplified exploded perspective view of an analytical test strip 100 according to an embodiment of the present invention. FIG. 2 is a simplified perspective view of the electrochemical-based analytical test strip of FIG. 1. FIG. 3 is a simplified perspective view of a portion of the electrochemical-based analytical test strip of FIG. 1 in contact with test meter electrical connector pins (ECP). FIG. 4 is a simplified side view of the portion of FIG. 3. FIG. 5 is a top view of a patterned spacer layer of the analytical test strip of FIG. 1. FIG. 6 is a top view of a third electrically conductive layer of the analytical test strip of FIG. 1.

Referring to FIGS. 1-6, analytical test strip 100 for use with a test meter in the determination of an analyte (such as glucose) in a bodily fluid sample (e.g., a whole blood sample) according to an embodiment of the present invention includes a first insulating layer 102 with a first insulating layer upper surface 104 and a first electrically conductive layer 106 disposed on first insulating upper surface 104. First electrically conductive layer 106 includes a first electrode portion 108 and an electrical contact pad 110 in electrical communication with first electrode portion 108.

Analytical test strip 100 also includes a patterned spacer layer 112 disposed above first electrically conductive layer 106. Patterned spacer layer 112 has a distal portion 114 defining a bodily fluid sample-receiving chamber 116 therein that overlies first electrode portion 108. Patterned spacer layer 112 also has an insulating proximal portion 118 with an upper surface 120 and a second electrically conductive layer 122 disposed thereon. Moreover, second electrically conductive layer 122 has an interlayer contact portion 124 and an electrical contact pad 126.

Analytical test strip 100 further includes a second insulating layer 128 disposed above patterned spacer layer 112. Second insulating layer 128 has a second insulating layer lower surface 130. Analytical test strip 100 yet further includes a third electrically conductive layer 132 disposed on second insulating layer lower surface 130 that includes a second electrode portion 134 and a proximal portion 136 that overlies interlayer contact portion 124. Second electrode portion 134 is disposed overlying and exposed to bodily fluid sample-receiving chamber 116 and in an opposing (i.e., co-facial) relationship to first electrode portion 108. Analytical test strip 100 also includes a reagent layer 138 (see FIG. 1 in particular).

In analytical test strip 100, the proximal portion of the third electrically conductive layer is operatively juxtaposed with the interlayer contact portion of the second electrically conductive layer such that there is an electrical connection between the second electrode portion of the third electrically conductive layer and the electrical contact pad of the patterned spacer layer during use of the analytical test strip. This electrical connection provides for unidirectional stacked electrical contact pads even though the first and second electrode portions are in an opposing (i.e., co-facial) arrangement.

The proximal portion of the third electrically conductive layer can be operatively juxtaposed with the inter layer contact portion by, for example, attachment with an electrically conductive adhesive or by compression of a gap therebetween (in the direction of arrow A of FIG. 4) upon insertion into the test meter. Such a compression can be achieved, for example, by the application of a force in the range of 3 pounds per square-inch to 30 pounds per square inch. The operative juxtaposition can be provided by any known means including an electrically fused joint or an electrically conductive foil connection.

Electrical contact pads 126 and 110 are each configured to operatively interface with a test meter via electrical contact with separate electrical connector pins (labeled ECP in FIGS. 3 and 4) of the test meter.

First insulating layer 102, insulating proximal portion 118, and second insulating layer 128 can be formed, for example, of a plastic (e.g., PET, PETG, polyimide, polycarbonate, polystyrene), silicon, ceramic, or glass material. For example, the first and second insulating layers can be formed from a 7 mil polyester substrate.

In the embodiment of FIGS. 1-6, first electrode portion 108 and second electrode portion 134 are configured to electro-chemically determine analyte concentration in a bodily fluid sample (such as glucose in a whole blood sample) using any suitable electrochemical-based technique known to one skilled in the art.

The first, second and third electrically conductive layers, 106, 122 and 132 respectively, can be formed of any suitable conductive material such as, for example, gold, palladium, carbon, silver, platinum, tin oxide, iridium, indium, or combinations thereof (e.g., indium doped tin oxide). Moreover, any suitable technique can be employed to form the first, second and third conductive layers including, for example, sputtering, evaporation, electro-less plating, screen-printing, contact printing, or gravure printing. For example, first electrically conductive layer 106 can be a sputtered palladium layer and third electrically conductive layer 132 can be a sputtered gold layer.

Distal portion 114 of patterned spacer layer 112 serves to bind together first insulating layer 102 (with first electrically conductive layer 106 thereon) and second insulating layer 128 (with third electrically conductive layer 132 thereon), as illustrated in FIGS. 1, 2, 3 and 4. Patterned spacer layer 112 can be, for example, a double-sided pressure sensitive adhesive layer, a heat activated adhesive layer, or a thermo-setting adhesive plastic layer. Patterned spacer layer 112 can have, for example, a thickness in the range of from about 50 micron to about 300 microns, preferably between about 75 microns and about 150 microns. The overall length of analytical test strip 100 can be, for example, in the range of 30 mm to 50 mm and the width can be, for example, in the range of 2 mm to 5 mm.

Reagent layer 134 can be any suitable mixture of reagents that selectively react with an analyte such as, for example glucose, in a bodily fluid sample to form an electroactive species, which can then be quantitatively measured at an electrode of analyte test strips according to embodiments of the present invention. Therefore, reagent layer 138 can include at least a mediator and an enzyme. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) using a pyrroloquinoline quinone (PQQ) co-factor, GDH using a nicotinamide adenine dinucleotide (NAD) co-factor, and GDH using a flavin adenine dinucleotide (FAD) co-factor. Reagent layer 134 can be formed using any suitable technique.

Figure 7:
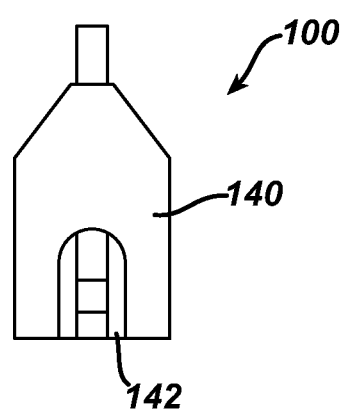
FIG. 7 is a simplified top view of the analytical test strip of claim 1 with an integrated carrier sheet.
Figure 8:
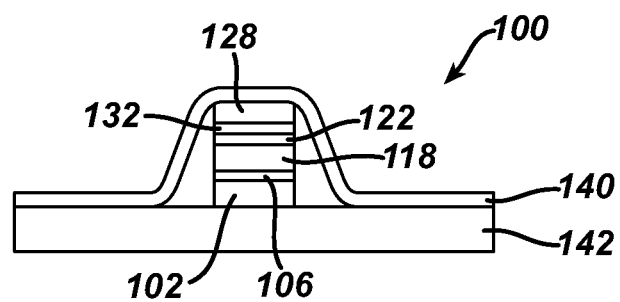
FIG. 8 is a simplified distal end view of the analytical test strip and integrated carrier sheet of FIG. 5
Figure 9:
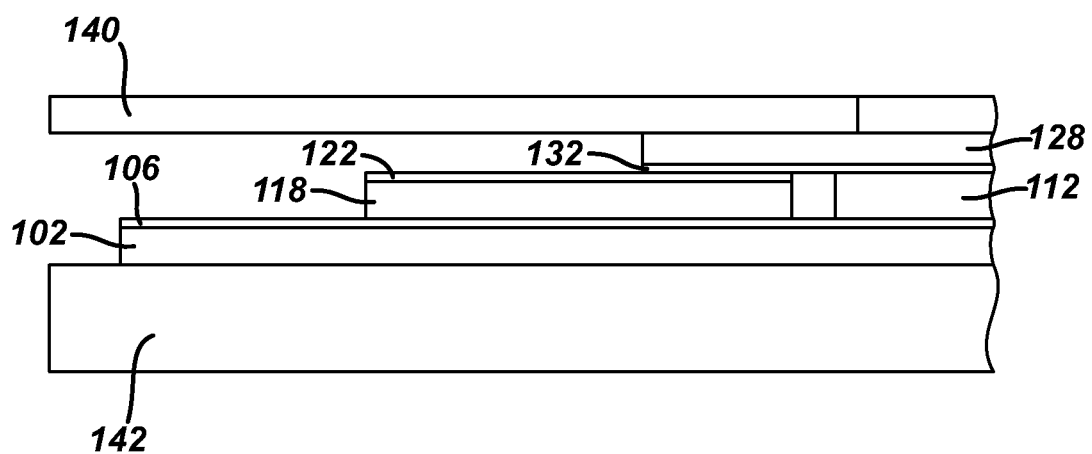
FIG. 9 is a simplified cross-sectional view of the analytical test strip and integrated carrier sheet of FIG. 5.

Referring to FIGS. 6, 7 and 8, if desired, analytical test strip 100 can further include at least one integrated carrier sheet configured solely as a user handle. In the embodiment of FIGS. 6-8, analytical test strip 100 includes a first integrated carrier sheet 140 and a second integrated carrier sheet 142. Moreover, a portion of the first insulating layer, first electrically conductive layer, patterned spacer layer, second insulating layer and second electrically conductive layer are disposed between first integrated carrier sheet 140 and second integrated carrier sheet1 142. First integrated carrier sheet 140 is configured such that the electrical contact pad of the first electrically conductive layer and the electrical contact pad of the patterned spacer layer are exposed. Such exposure enables electrical contact to a test meter during use.

The first and second integrated carrier sheets can be formed of any suitable material including, for example, paper, cardboard, or plastic materials. Since the first and second integrated carrier sheets are configured solely as a user handle in the present embodiments, they can be formed of relatively inexpensive materials.

Figure 10:
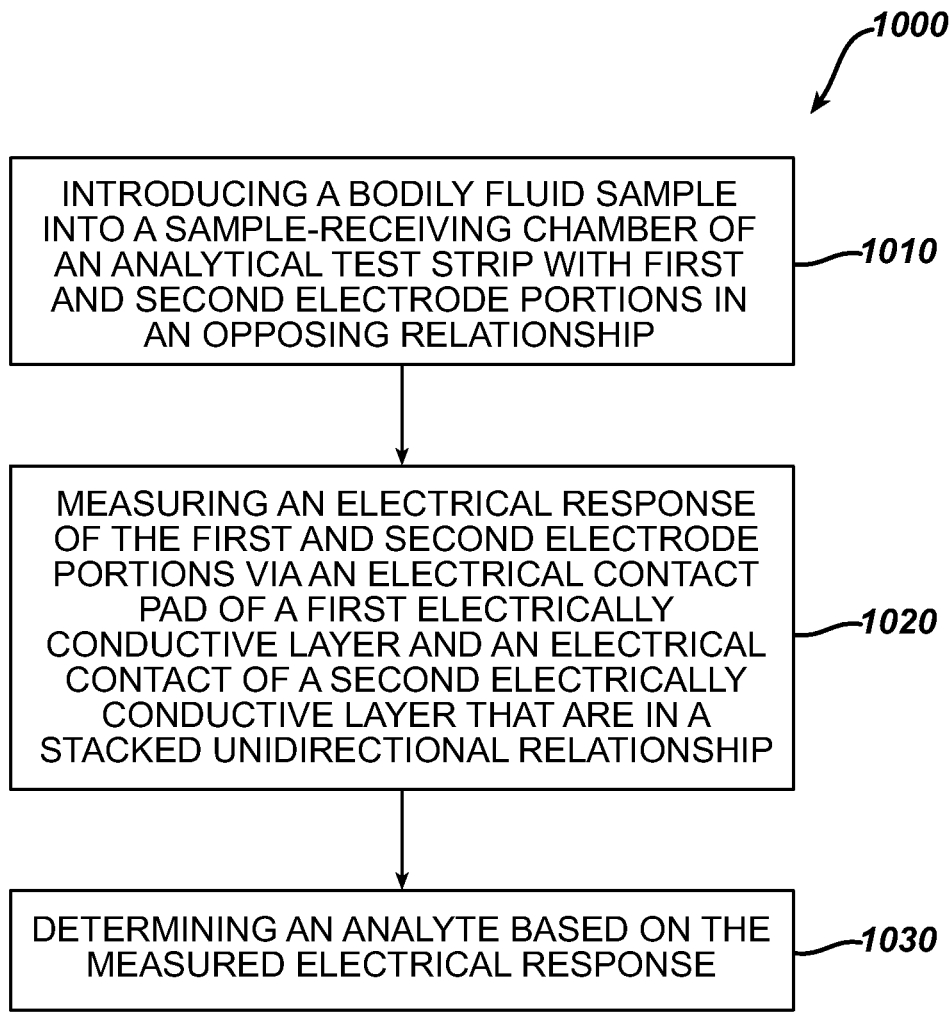
FIG. 10 is a flow diagram depicting stages in a method for determining an analyte in a bodily fluid sample according to an embodiment of the present invention.

FIG. 10 is a flow diagram depicting stages in a method 1000 for determining an analyte (such as glucose) in a bodily fluid sample (for example, a whole blood sample). Method 1000 includes introducing a bodily fluid sample into a sample-receiving chamber of an analytical test strip that has a first electrode portion of a first electrically conductive layer and a second electrode portion of a third electrically conductive layer therein (see step 1010 of FIG. 10). In addition, the first electrode portion and the second electrode portion are in an opposing relationship.

At step 1020 of method 1000, an electrical response of the first electrode portion and the second electrode portion is measured via an electrical contact pad of the first electrically conductive layer and via an electrical contact pad of a second electrically conductive layer of a patterned spacer layer of the analytical test strip. The patterned spacer layer is disposed between the first electrically conductive layer and the third electrically conductive layer. Furthermore, the electrical contact pad of the first electrically conductive layer and the second electrically conductive layer are configured in a unidirectional stacked relationship and the second electrode portion is in electrical communication with the electrical contact pad of the second electrically conductive layer.

Method 1000 also includes, at step 1030, determining the analyte based on the measured electrical response.

Once apprised of the present disclosure, one skilled in the art will recognize that method 1000 can be readily modified to incorporate any of the techniques, benefits and characteristics of analytical test strips according to embodiments of the present invention and described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. An analytical test strip, for use with a test meter, the analytical test strip comprising:
   a first insulating layer with a first insulating layer upper surface;
   a first electrically conductive layer disposed on the first insulating layer upper surface and including:
      a first electrode portion; and
      at least one electrical contact pad in electrical communication with the first electrode portion;
   a patterned spacer layer disposed above the first electrically conductive layer and including:
      a distal portion defining a bodily fluid sample-receiving chamber therein that overlies the first electrode portion; and
      an insulating proximal portion with an upper surface and a second electrically conductive layer disposed thereon, the second electrically conductive layer including:
         an interlayer contact portion; and
         an electrical contact pad;
   a second insulating layer disposed above the patterned spacer layer and having a second insulating layer lower surface;
   a third electrically conductive layer disposed on the third insulating layer lower surface and including:
      a second electrode portion; and
      a proximal portion overlying the interlayer contact portion,
   wherein the second electrode portion is disposed overlying and exposed to the sample-receiving chamber and in an opposing relationship to the first electrode portion,
   wherein the proximal portion of the third electrically conductive layer is operatively juxtaposed with the interlayer contact portion of the second electrically conductive layer such that there is an electrical connection between the second electrode portion of the third electrically conductive layer and the electrical contact pad of the patterned spacer layer during use of the analytical test strip,
   wherein the analytical test strip includes a first integrated carrier sheet and a second integrated carrier sheet, and
   wherein at least a portion of the first insulating layer, first electrically conductive layer, patterned spacer layer, second insulating layer and second electrically conductive layer are disposed between the first integrated carrier sheet and the second integrated carrier sheet.

2. The analytical test strip of claim 1 wherein one of the first integrated carrier sheet and the second integrated carrier sheet is configured such that the electrical contact pad of the first electrically conductive layer and the electrical contact pad of the patterned conductor layer are exposed.

3. The analytical test strip of claim 1 wherein the electrochemical-based analytical test strip is configured for the determination of an analyte in a bodily fluid sample.

4. The analytical test strip of claim 3 where the analyte is glucose.

5. The analytical test strip of claim 3 wherein the bodily fluid sample is a whole blood sample.

* * * * *